United States Patent [19]
van de Veen

[11] Patent Number: 5,888,236
[45] Date of Patent: Mar. 30, 1999

[54] PIVOT DEVICE BETWEEN PARTS OF AN ORTHOPEDIC AID

[75] Inventor: Paul Gerad van de Veen, Enschede, Netherlands

[73] Assignee: Otto Bock Orthopadische Industrie Besitz und Verwaltungs Kommanditgesellschaft, Duderstadt, Germany

[21] Appl. No.: 787,572

[22] Filed: Jan. 22, 1997

Related U.S. Application Data

[62] Division of Ser. No. 454,691, May 31, 1995, Pat. No. 5,645,590.

[30] Foreign Application Priority Data

Nov. 25, 1994 [NL] Netherlands ............... 94 01975

[51] Int. Cl.$^6$ ............................................. A61F 2/64
[52] U.S. Cl. .............................. 623/44; 623/46; 403/116
[58] Field of Search ................................. 403/116, 117, 403/113, 112; 623/43–46, 39; 602/16, 26

[56] References Cited

U.S. PATENT DOCUMENTS

| | | | |
|---|---|---|---|
| 2,599,297 | 6/1952 | Touson | 623/46 |
| 4,005,496 | 2/1977 | Wilkes | 623/44 |
| 4,522,528 | 6/1985 | Bewers | 403/61 |
| 5,181,931 | 1/1993 | van de Veen | 623/40 |
| 5,314,498 | 5/1994 | Gramnas | 623/39 |

FOREIGN PATENT DOCUMENTS

| | | | |
|---|---|---|---|
| 188849 | 2/1957 | Austria | 623/39 |
| 0 439 028 A3 | 7/1991 | European Pat. Off. . | |
| 735844 | 5/1943 | Germany . | |
| 2841999 | 4/1980 | Germany | 623/46 |
| 4325655 | 2/1995 | Germany | 602/16 |
| 274375 | 8/1951 | Switzerland . | |
| 1138151 | 2/1985 | U.S.S.R. | 623/39 |

*Primary Examiner*—David H. Willse
*Attorney, Agent, or Firm*—Whitham, Curtis & Whitham

[57] ABSTRACT

The invention relates to a device producing a stance flexion. This goal is achieved according to the invention by virtue of the fact that in the initial position of the multi-element joint system one element (joint element) can execute two movements with respect to the other elements (joint elements) connected to it, with at least one movement, after its initiation, at least predominantly blocking the other possible movement.

2 Claims, 14 Drawing Sheets

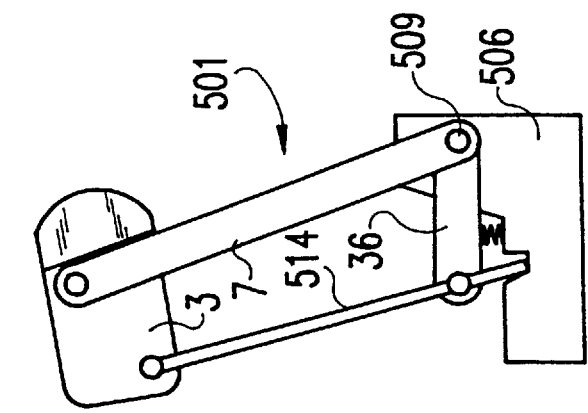
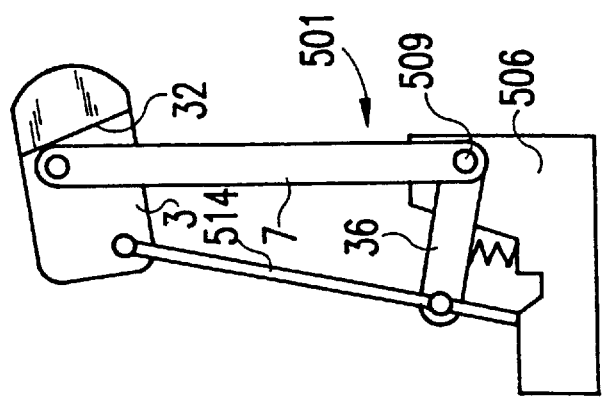
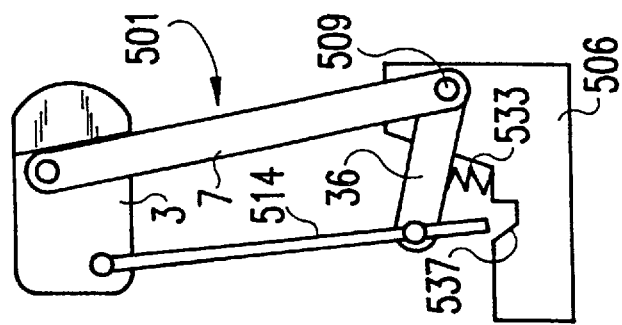

PIVOT DEVICE BETWEEN PARTS OF AN ORTHOPEDIC AID

CROSS REFERENCE TO RELATED APPLICATION

This application is a divisional of application Ser. No. 08/454,691 filed May 31, 1995, now U.S. Pat. No. 5,645,590.

BACKGROUND OF THE INVENTION

1. Field of the Invention

The invention relates to a pivot device between parts of an orthopedic aid, for example a prosthetic knee for leg amputees, comprising a multi-element kinematic joint chain with at least four joint members, in which the members connected with one another have a common rotational axis, and these rotational axes extend essentially parallel to one another.

2. Description of the Prior Art

The use of multi-element joint systems for replacement or reinforcement of joint function in orthopedic aids has already been known for a long time and is frequently employed because of the advantages that such a mechanism enjoys over more conventional mechanisms with a single fixed pivot (center of rotation). These advantages include among others an improved following or improved imitation, in comparison to a single-axis joint mechanism, of a natural movement of the limbs and an increased or better-controllable joint stability under load and are achieved by a suitable choice of the dimensions of the members of the joint system and their positions with respect to one another. In particular, when a multi-element joint system is used to replace or reinforce the knee function, the latter aspect is of great significance. At the beginning of a step, when the heel touches the ground and the joint mechanism in the extended position is loaded by the weight of the user, it is important that the mechanism not bend immediately because the user would then have no support for the body and would fall. This can be prevented in a single-axis joint mechanism only by using a complex and less reliable brake mechanism.

In a multi-element joint system this property on the other hand can be achieved by choosing the joint geometry in such fashion that in the extended state of the joint mechanism, the virtual rotational point around which pivots the lower leg or the part of the leg prosthesis that replaces the lower leg, lies behind the line of application that connects the two loading points, namely the heel and the hip joint.

By a suitable choice of the geometry of the multi-rod mechanism, it is also possible to ensure that the virtual point of rotation of a stepping movement is located such that the prosthesis or "orthosis" can be brought into a forwardly pivoting movement more simply in comparison to a single-axis mechanism. The great stability to be achieved at the beginning of a stepping movement, the easily conferred backward swinging movement, and the possibility of finding a good compromise between these two properties in a simple fashion make the multi-rod mechanism suitable simply for replacement or for reinforcement of a joint function.

An important requirement for a kinematic multi-rod mechanism in such applications is that it have an initial deflecting bend under load, as for example the human knee joint also does under load. The cushioning effect of this initial deflecting bending of the joint under loading of the leg prevents a jerky gait which can be uncomfortable for the user and even painful with time. The initial bending of the joint also prevents a limitation of the vertical movement of the center of gravity of the body so that the energy required for walking remains limited. This knee bending is referred to as "stance flexion."

The existing pivoting devices between parts of an orthopedic aid, for example a prosthesis for leg amputees, suffer from at least one of the following disadvantages:

They do not exhibit the properties described at all.

They possess the described properties only to a slight extent. This is the case when the stance flexion that occurs in practice is no greater than 3° to 4° which is too limited for the described advantages of stance flexion to be completely realized.

They produce the described properties by using a multi-element joint system with two degrees of freedom, both of which can be understood as the above-mentioned pivoting movement of the mechanism, with the movement taking place according to a single degree of freedom against the spring force of an elastic element and with the two degrees of freedom influencing one another mutually, but nevertheless being independent of one another. These mechanisms have the disadvantage that the exchange of stored spring energy between these degrees of freedom is always possible, and this is perceived by the user as an extremely unpleasant effect so that additional means, for example dissipative elements, are required in order to convert this spring energy into heat by dissipation.

They provide the described properties by using a multi-element joint system with only a single degree of freedom and one turning point in the pivoting movement, which is achieved by virtue of the fact that in the extension of one of the members of the multi-element joint system a second member or a push-on connection is provided that makes such mechanisms relatively long.

SUMMARY OF THE INVENTION

The goal of the invention is to provide a device that provides a stance flexion that is so large that the advantages of stance flexion as possessed by the natural knee joint are fully realized.

In addition, the invention has the goal of achieving this task without the above-mentioned disadvantages of existing devices.

Another goal of the invention is to provide a device that combines simple design with high reliability.

To achieve these goals, the invention provides a device of the species recited at the outset characterized by the fact that in the initial position of the multi-element joint system, one element (joint element) can execute two movements with respect to the other elements (joint elements) connected with it, with at least one movement, following its initiation, blocking the other possible movement at least predominantly.

The device according to the invention produces the desired flexibility and relatively great stance flexion in connection with preventing the second degree of freedom of movement and with a relatively small and simply produced mechanism at that.

It must be emphasized that the term "movement" used here must be understood either as pure rotation or pure translation or as any fixed combination of a rotation with a translation. In other words, the term "movement" describes/comprises the movement according to a single typical degree of freedom of movement of the joint mechanism.

The additional spring element to for example can be used to bring the lower leg slightly forward to end the swing phase.

BRIEF DESCRIPTION OF THE DRAWINGS

Additional features of the invention will be explained with reference to the embodiments of the invention shown in the following figures, but is not limited to them.

DETAILED DESCRIPTION OF THE PREFERRED EMBODIMENTS OF THE INVENTION

Figure 1:
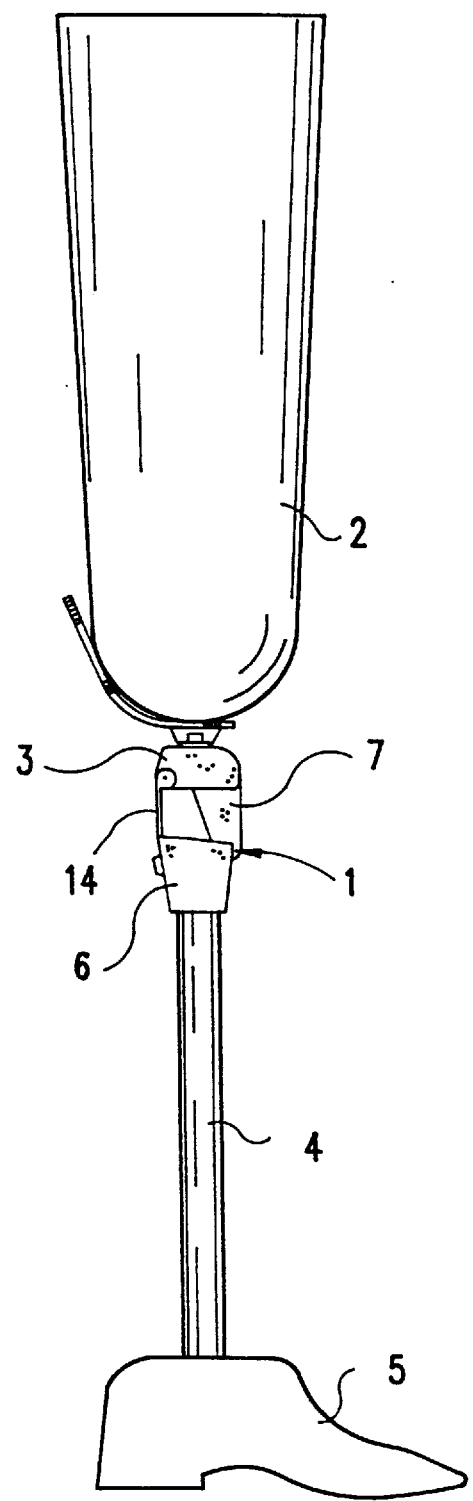
FIG. 1 is a side view of a prosthetic knee joint according to the invention, located between an artificial upper leg and an artificial lower leg.

FIG. 1 shows a prosthetic knee joint 1, a first part 3 connected with an artificial upper leg 2, and a lower part 6 connected with an artificial lower leg 4 with foot 5. The prosthetic knee joint 1 also includes a kinematic joint chain, described below, to which parts 3 and 6 belong.

The rotational axes (pivot joints) 8, 9, 10, 11 are all essentially parallel to one another and define a movement plane that runs perpendicularly to them.

Figure 2:
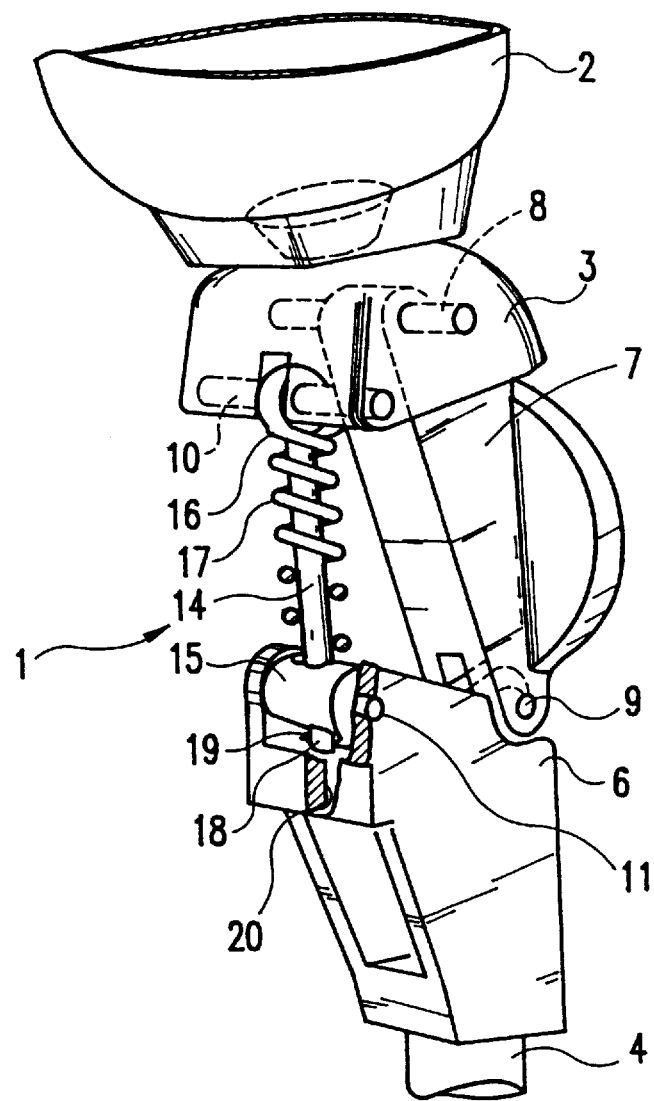
FIG. 2 shows the prosthetic knee joint according to FIG. 1 on an enlarged scale and with a partially cut-away perspective view.
Figure 3:
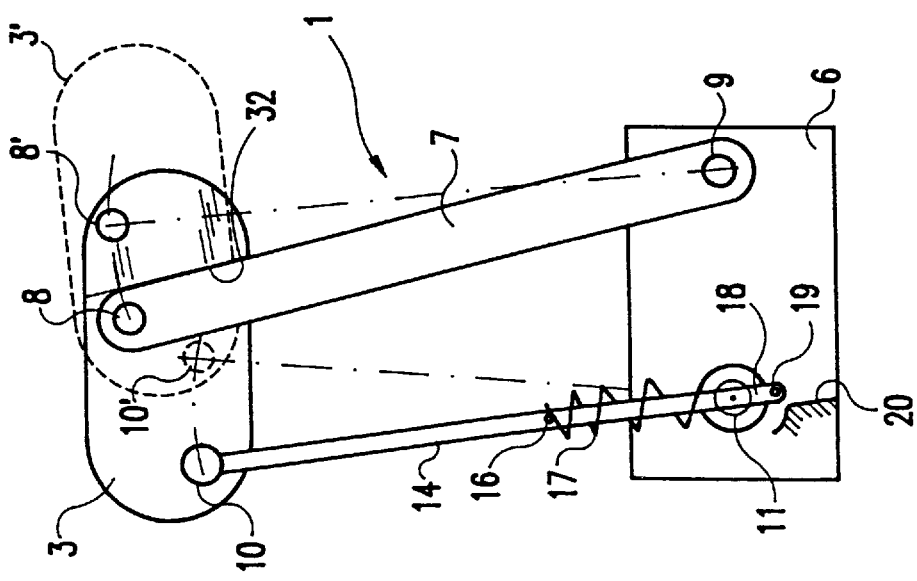
FIG. 3 is a schematic diagram showing a side view of the prosthetic knee joint according to FIG. 2 in the resting state.

A guide block 15 is connected with rotational axis 11 with articulation, in which block rear joint element 14 is slidably guided. Between block 15 and a bead 16 provided on joint element 14 a compression spring 17 is provided. This compression spring presses joint element 14 upward in such fashion that, as a result, a resting position of upper part 3 with respect to lower part 6 is determined. In this unloaded resting state shown schematically in FIG. 2, the upper part 3 is freely pivotable with respect to lower part 6. As an example, rotated positions of the rotational axes (pivot joints) 10 and 8 are represented by broken lines and labeled (in FIG. 3) 10' and 8', respectively.

Figure 4:
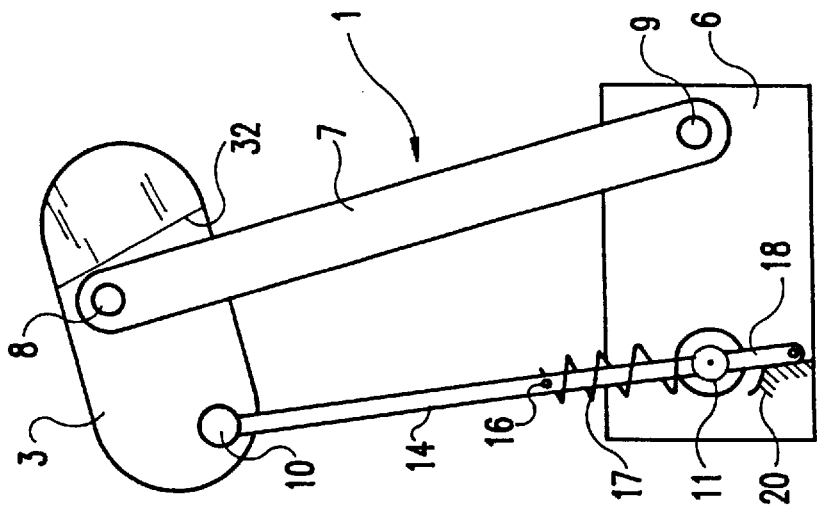
FIG. 4 is a view corresponding to FIG. 3 showing the prosthetic knee joint under a weight load.

FIG. 4 shows the situation in which, under a weight load, rear joint element 14 has been moved downward against the action of compression spring 17. In this position, end area 18 cooperates with a stop surface 20 on lower part 6. As a result the rotational degree of freedom shown in FIG. 3 by the broken lines is blocked.

It should be noted that end area 18 has a cross pin 19 that prevents joint element 14 leaving block 15 under the influence of spring 17.

Figure 5:
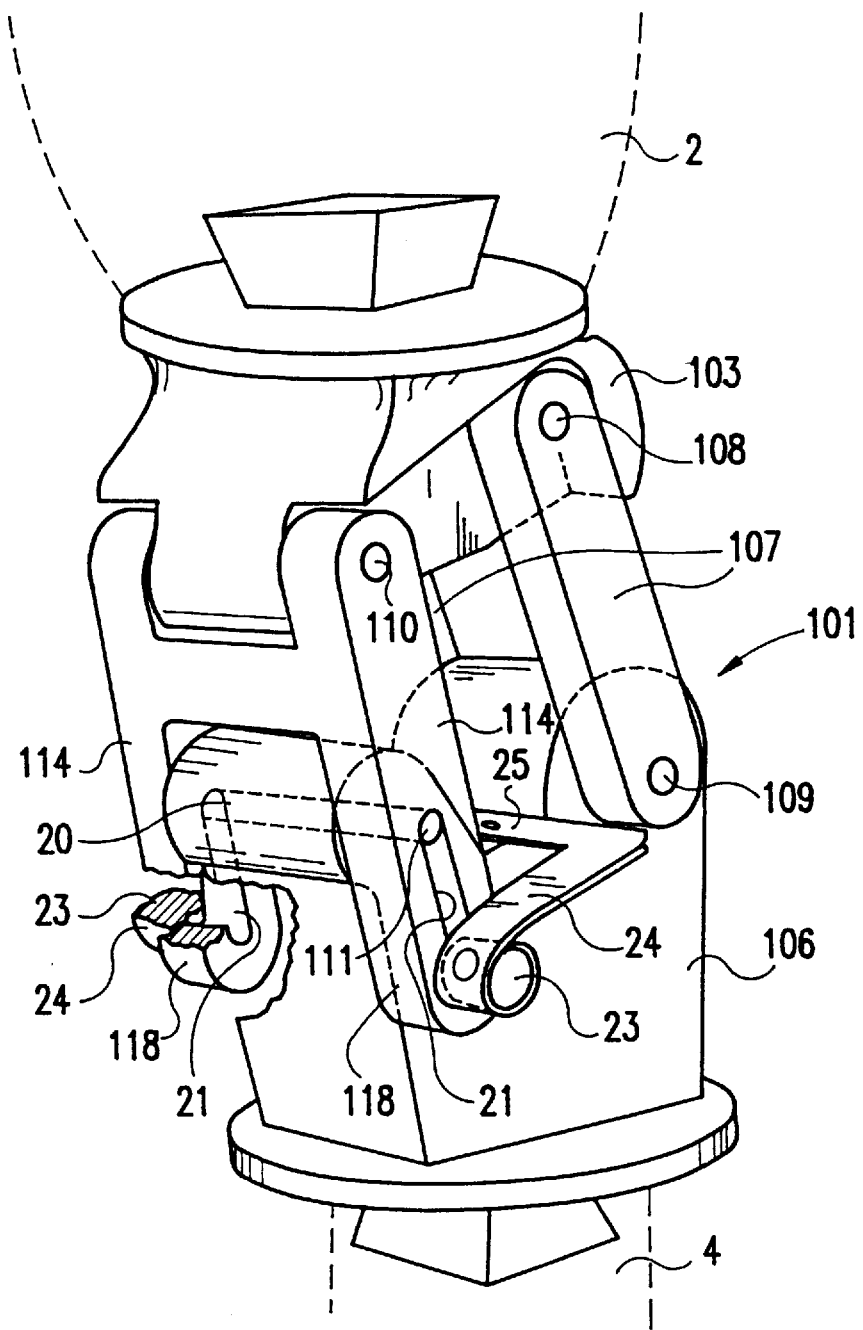
FIG. 5 is a partially cut-away perspective view of a variation in the loaded state.
Figure 7:
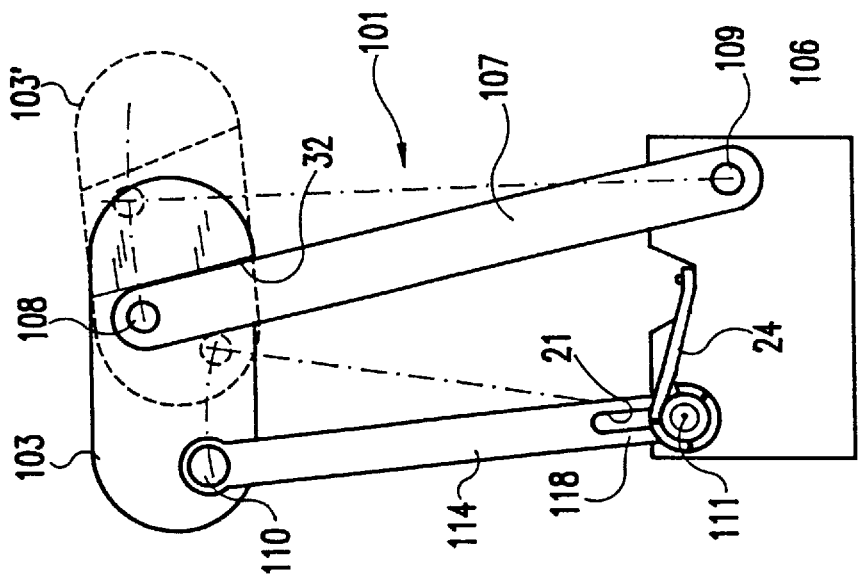
FIG. 7 is a view of the prosthetic knee joint, corresponding to FIG. 6, in the unloaded state.
Figure 6:
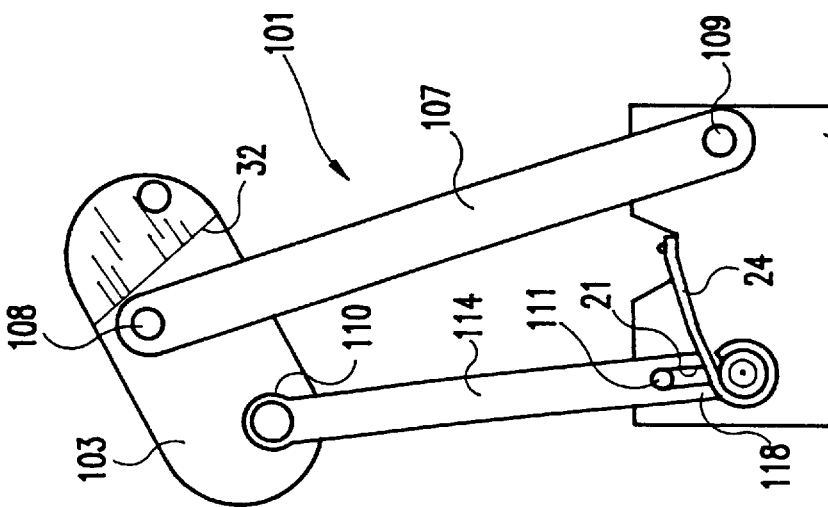
FIG. 6 is a view of the prosthetic knee joint according to FIG. 5 corresponding to FIG. 4 in the loaded state.

FIGS. 5, 6, and 7 show a variation. Prosthetic knee joint 101 comprises an upper part 103, a lower part 106, two front joint elements 107, and two rear joint elements 114 coupled to one another. The individual joints are labeled 108, 109, 110, and 111. In contrast to prosthetic knee joint 1, lower part 106 has a cross pin 20, displaceably mounted in an elongate hole 21 in rear joint element 114. This arrangement corresponds functionally with the guidability of the rear joint element 14 in block 15 in FIGS. 1–4.

End area 118 bears a pin 23 on which the eye-shaped end of a leaf spring is mounted. The leaf spring is connected with a fastening part 25 with lower part 106. It acts not only as a return spring to move prosthetic knee joint 101 into the resting position shown in FIG. 7, but also as a guide arm by which pin 23 and hence end area 118 is forced into a predetermined path; in this way, the rotational degree of freedom shown in FIG. 7 by the dashed lines is locked in the position shown in FIGS. 5 and 6. The position shown in FIGS. 5 and 6 is achieved under weight load, especially when a user is standing on the leg prosthesis provided with the prosthetic knee joint.

Figure 8:
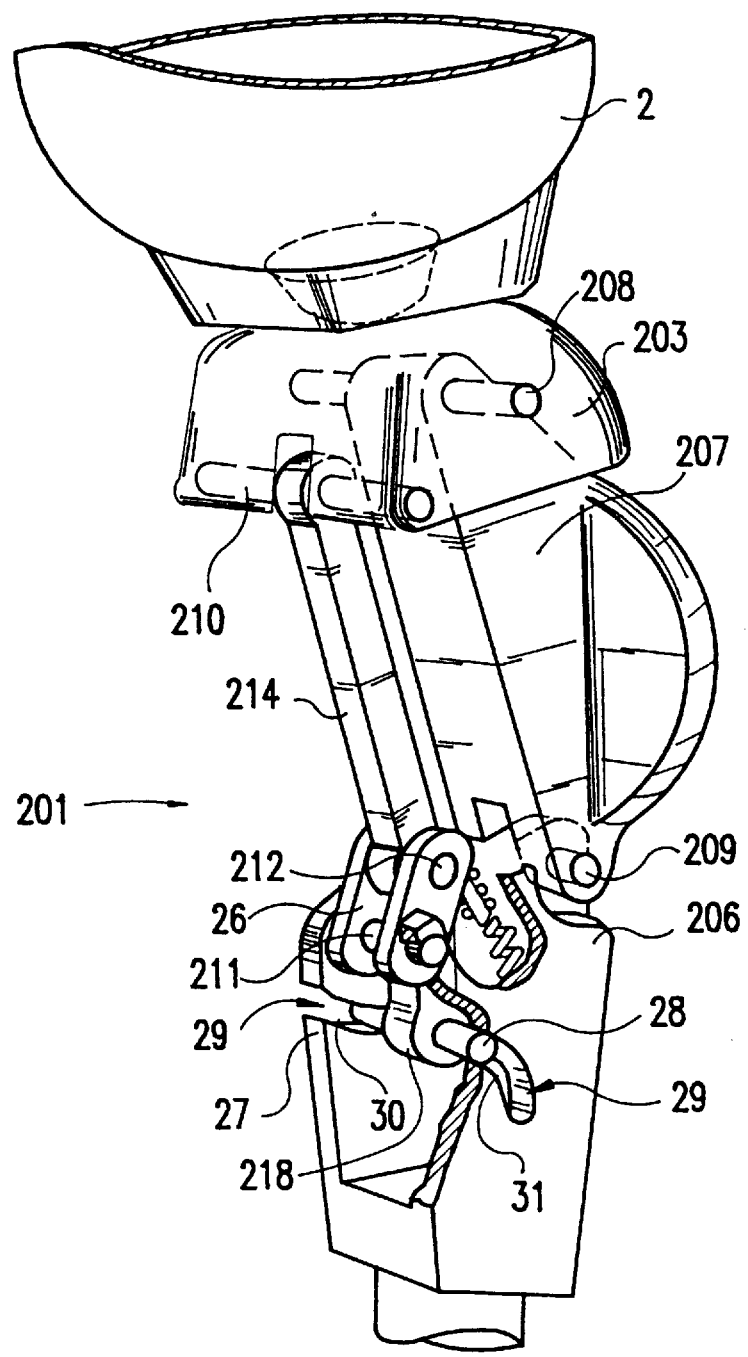
FIG. 8 is another modified design in a partially cut-away perspective view in the state without a weight load.
Figure 10:
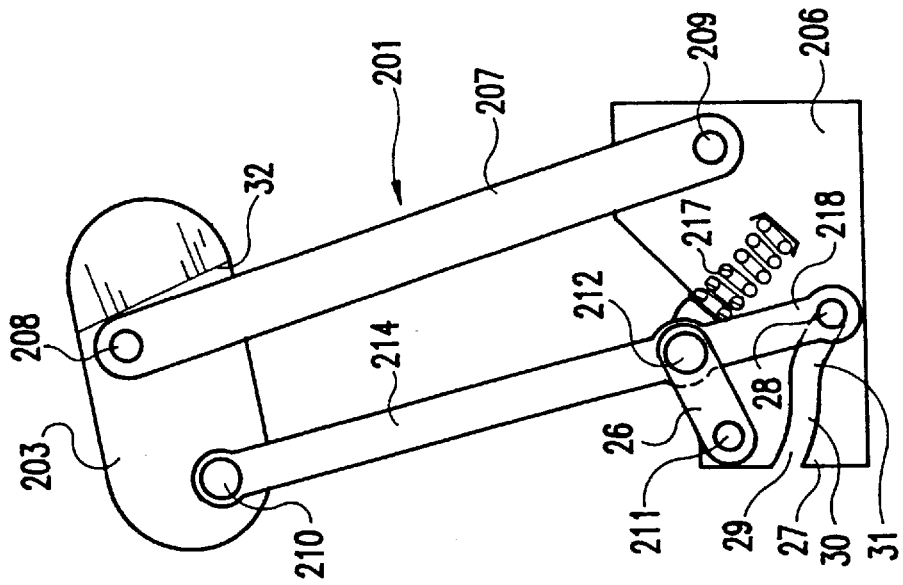
FIG. 10 is a view of the prosthetic knee joint according to FIG. 8, corresponding to FIG. 9, under weight load.
Figure 9:
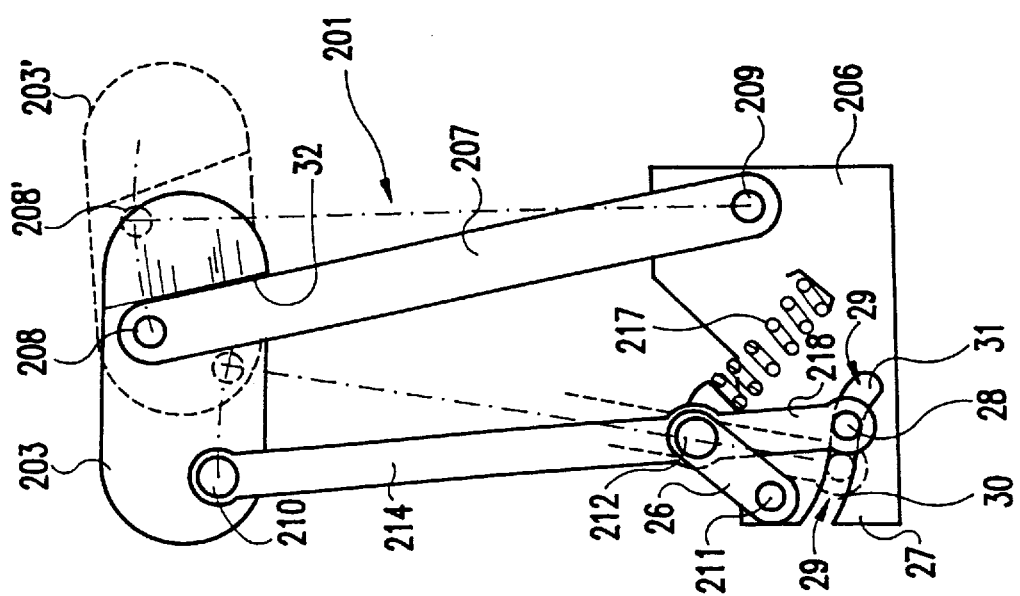
FIG. 9 is a view of the prosthetic knee joint according to FIG. 8 corresponding to FIGS. 3 and 7 in the resting state.

FIGS. 8, 9, and 10 show a prosthetic knee joint 201. This comprises an upper part 203 and a lower part 206 connected together by a front joint element 207 and a rear joint element 214. The respective rotational axes (pivot joints) that correspond to the axes (joints) 8, 9, 10, 11 in FIGS. 1–4 and axes (joints) 108, 109, 110, 111 in FIGS. 5–7, are marked 208, 209, 210, and 211.

In prosthetic knee joint 201, rear joint element 214 is connected with articulation with a guide arm 26 by means of a fifth rotational axis 212, said arm being connected by means of a fourth rotational axis 211 with rear area 27 of lower part 206. Free end area 218 of rear joint element 214 bears a cross pin 28, guided in elongate holes 29 in lower part 206.

As in the embodiments described above, this joint element arrangement with additional guidance ensures that in the free state shown in FIGS. 8 and 9, achieved by a compression spring 217, a free rotation around rotational axes 208, 209, 210, and 212 is ensured. A rotated state of upper part 203 is shown by broken lines. With a weight load, upper part 203 moves downward thus compressing compression spring 217. As a result, cross pin 28 is moved into the right part of elongate hole 29. In this connection it should be pointed out that left part 30 has a curvature whose center of curvature forms rotational axis 212. This left part 30 abuts right part 31 in a yielding manner.

All three embodiments of the prosthetic knee joint according to the invention have in common an extension stop 32 mounted on upper part 3, 103, or 203 and cooperating with the upper part of front joint element 7, 107, 207.

Figure 12:
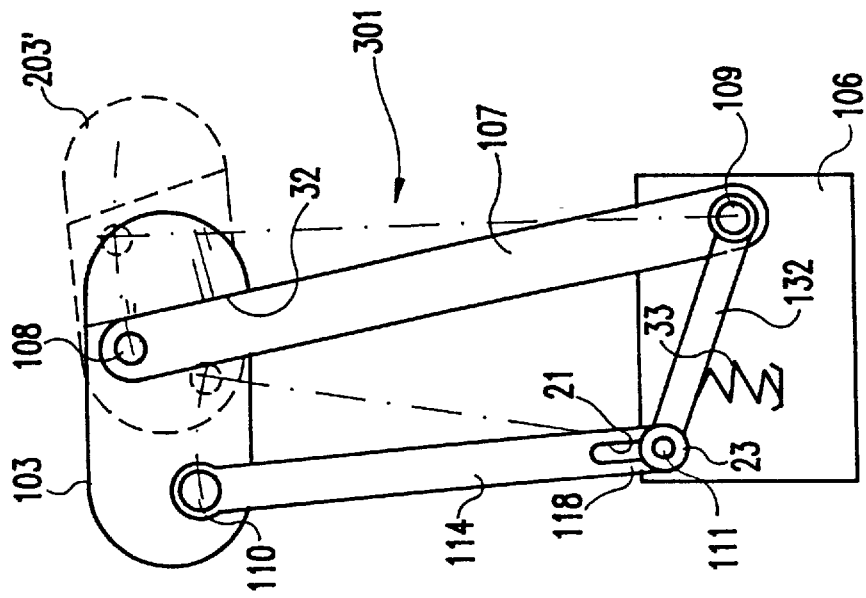
FIG. 12 is a view corresponding to FIG. 11 showing the prosthetic knee joint under a weight load.
Figure 11:
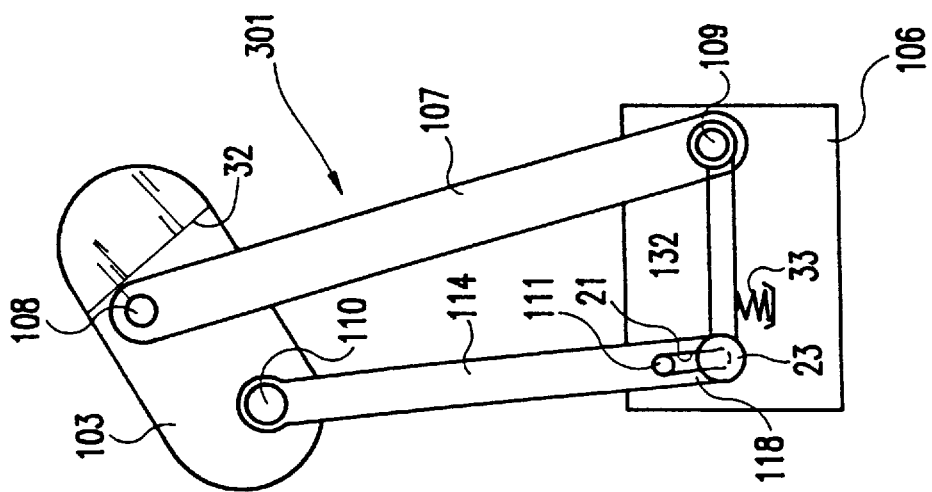
FIG. 11 is a view of a variation that corresponds with FIG. 6.

FIGS. 11 and 12 show a prosthetic knee joint 301 in two positions corresponding to FIGS. 6 and 7. In this embodiment leaf spring 24 according to FIGS. 5, 6, and 7 is replaced by an arm 132 located between the second rotational axis and pin 23, as well as a compression spring 33 located between arm 132 and lower part 106.

Figure 13:
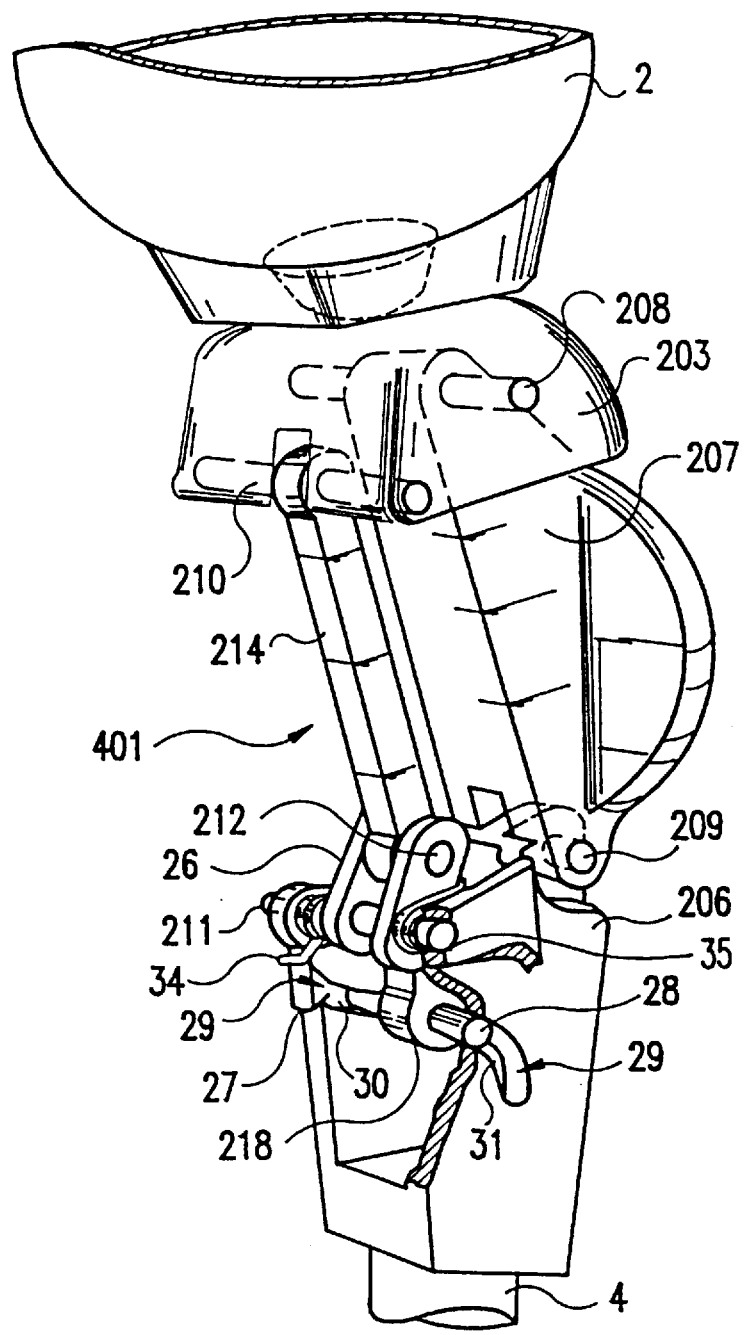
FIG. 13 is a schematic perspective view showing an additional embodiment of the present invention FIGS. 14, 15, 16; 17, 18, 19; 20, 21, 22; 23, 24, 25; 26, 27, 28 are schematic side views showing five additional embodiments each in three states.

FIG. 13 shows a view corresponding to FIG. 8 of a prosthetic knee joint 401. In contrast to the embodiment shown in FIG. 8 the return of the prosthetic knee joint 401 is produced by torsion springs 34, 35 which, like compression spring 217, in prosthetic knee joint 201 have the function of moving arm 26 from a compressed state (see FIG. 10) into the more upwardly directed position (see FIGS. 8 and 9). Torsion springs 34 and 35 act between lower part 206 and arm 26.

FIGS. 14, 15, 16; 17, 18, 19; 20, 21, 22; and 23, 24, 25 show four different prosthetic knee joints 501, 601, 701, and 801 in three different positions, namely in the starting position, in the position after "movement 1" or the "swing flexion", and in the position after "movement 2" or "stance flexion."

The individual positions require no further explanation in view of the above detailed descriptions of the embodiments in question. Therefore, the following remarks will be limited to a discussion of important differences.

Prosthetic knee joint 501, according to FIGS. 14, 15, and 16, is made so that rear joint element 514 is coupled by means of arm 36, with which it is articulated, with rotational axis 509. Spring 533 acts on arm 36. The free lower end of rear joint element 514 cooperates with guide surface 537.

Figure 19:
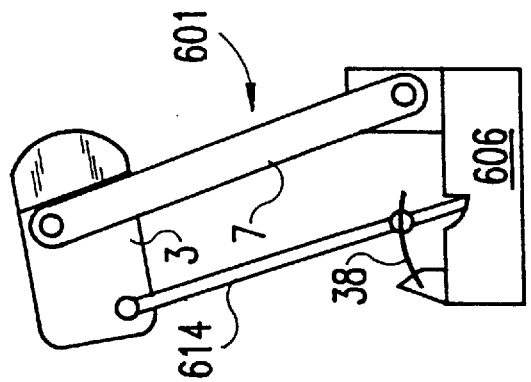
Figure 18:
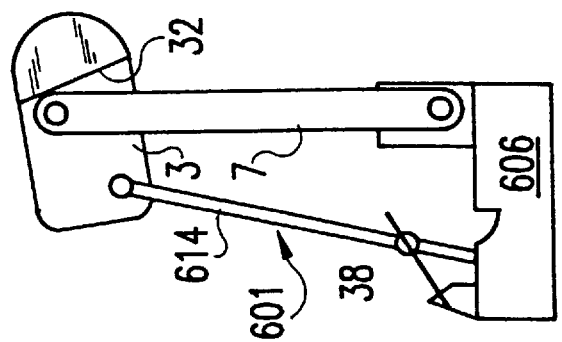
Figure 17:
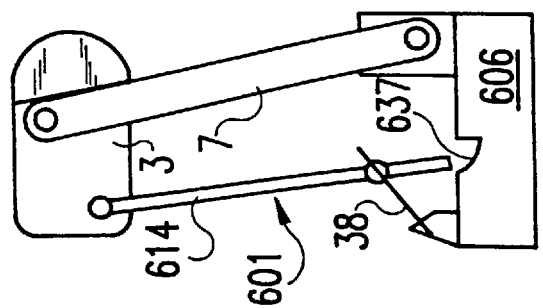

In prosthetic knee 601 according to FIGS. 17, 18, and 19 a leaf spring 38 is used that is connected permanently with lower part 606 and articulated with rear joint element 614 at a fixed position. The lower end of rear joint element 614 cooperates with a guide surface 637.

Figure 22:
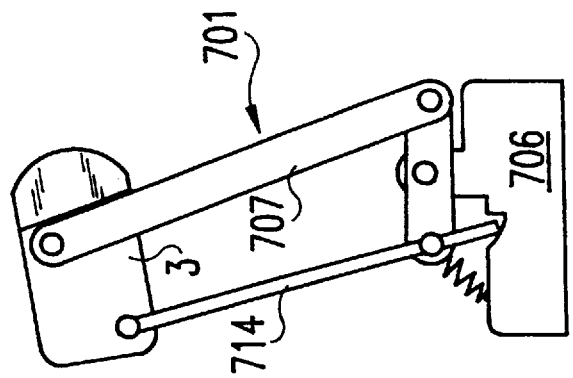
Figure 21:
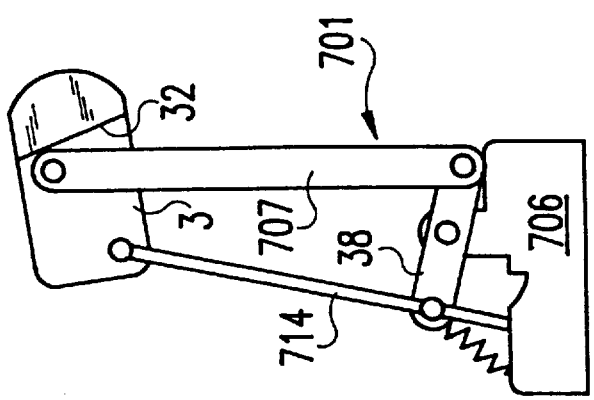
Figure 20:
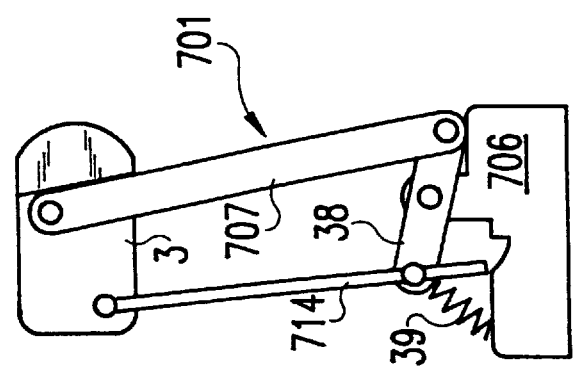

The prosthetic knee joint according to FIGS. 20, 21, and 22 has the special feature that the forward joint element 707 is not coupled directly with lower part 706. Instead, a tilt arm 38 is used here which is connected by its central part with lower part 706, by its front area with front joint element 707, and by its rear area with rear joint element 714. Tilt arm 38 is brought by a compression spring 39 into the resting position or starting position shown in FIG. 20.

Figure 25:
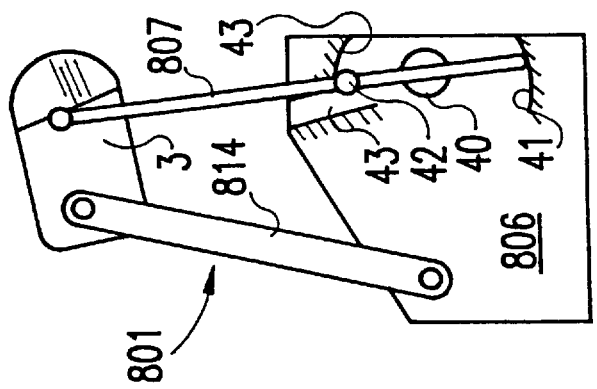
Figure 24:
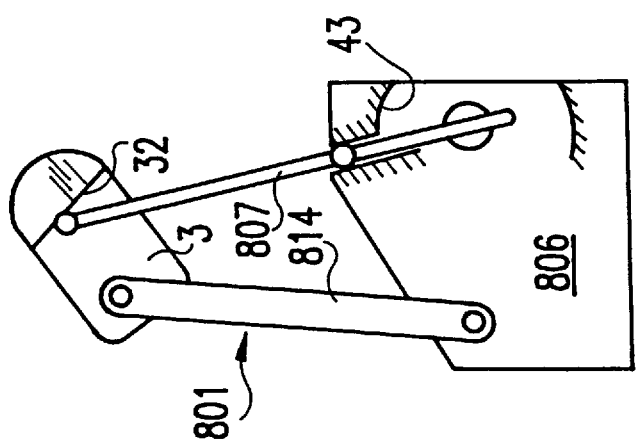
Figure 23:
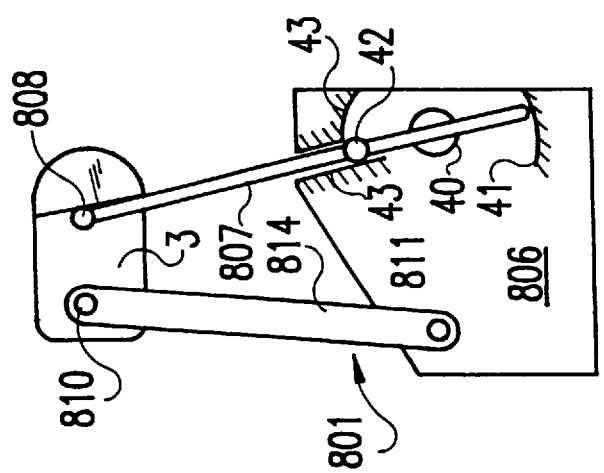

Prosthetic knee joint 801 according to FIGS. 23, 24, and 25 has the special feature that rear joint element 814 is connected by rotational axes 810 and 811 with upper part 3 or with lower part 806. Front joint element 807 is connected by rotational axis 808 with upper part 3. Joint element 807 is guided in slide joint 40, connected with lower part 806. The lower end of joint element 807 cooperates with guide surface 41. A guide element permanently connected with front joint element 807 cooperates with guide surfaces that are all labeled 43.

Figure 28:
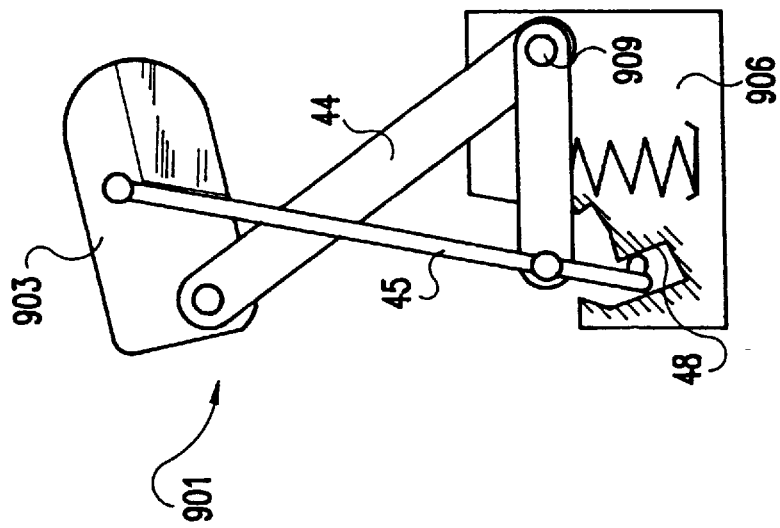
Figure 27:
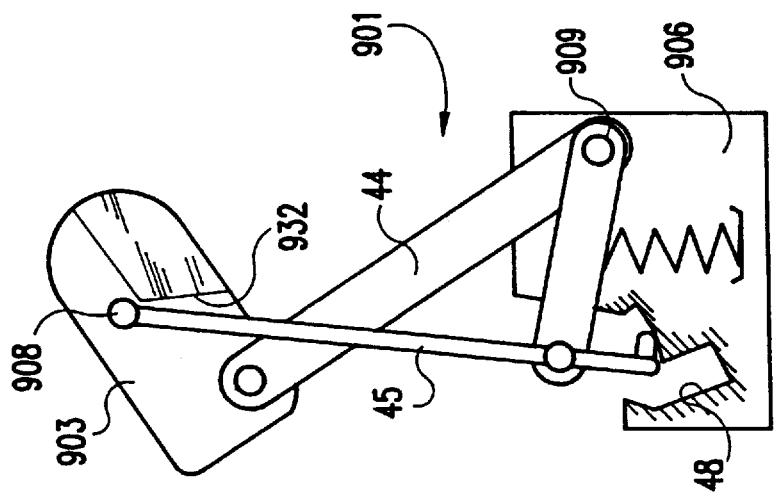
Figure 26:
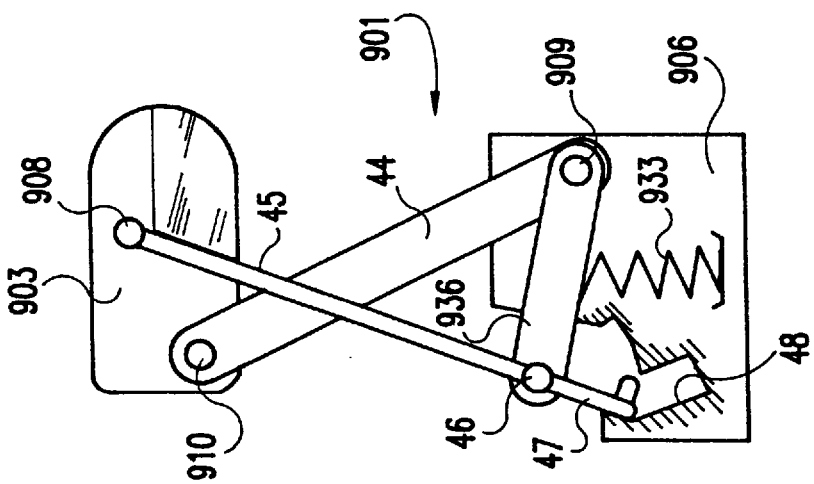

Prosthetic knee joint 901 according to FIGS. 26, 27, and 28 comprises a lower part 906 and an upper part 903. In contrast to all of the embodiments shown and described above, knee joint 901 comprises two joint elements 44, 45 which, as the figures clearly show, cross in the area between parts 903 and 906. Joint element 44 is connected by means of a front joint 909 with lower part 906 and by a rear joint 910 with upper part 903. Joint element 45 is connected by means of a front joint 908 with upper part 903. An arm 936 utilizes the rotational axis of joint 909 and is connected by joint 46 with the lower area of joint element 45. End area 47 of joint element 45 cooperates with guide surfaces 48 in lower area 906. A return spring 933 is shown schematically.

It should be noted that for reasons of schematic representation, the indication of spring means has been eliminated at several points. However, it should be clear that they can be mounted in any suitable position between parts of the pivot connection according to the invention connected with one another. Similarly, this likewise applies to the damping devices.

Finally, it should be pointed out that functionally corresponding parts in the individual embodiments are characterized uniformly, with the number of the respective embodiment being placed before the respective numeral.

While the invention has been described in terms of its preferred embodiments, those skilled in the art will recognize that the invention can be practiced with modification within the spirit and scope of the appended claims.

I claim:

1. A pivot device for use between parts of an orthopedic aid, comprising:

a multi-element kinematic joint chain having at least four joint elements, and rotation means connecting respective ones of said joint elements, wherein the elements connected with one another have a common rotational axis, and said rotation means are positioned parallel to one another, wherein said joint chain includes at least a first position representing full extension, said first position provides at least two different modes of joint flexion, in said first position, a first element of said joint elements performs a first type of movement and a second type of movement with respect to remaining joint elements of said joint elements connected to a first side of said first element, wherein said first type of movement, when initiated before said second type of movement, blocks said second type of movement and said second type of movement, when initiated before said first type of movement, blocks said first type of movement, a front joint element of said joint elements pivotally coupled with an upper connecting joint element and a lower connecting joint element, a pivoting movement of the front joint element is substantially limited by at least one stop, a rear joint element of said joint elements being positioned substantially behind the front joint element in a walking direction, the rear joint element is pivotally connected at one end with the upper connecting joint element and at the other end with the lower connecting joint element so that the rear joint element in a starting position can perform a parallel displacement and a pivoting movement with respect to the lower connecting joint element, a coupling element connected with the lower connecting joint element, a spring element, and at least a second stop positioned proximate to the spring element, the spring element and the at least second stop counteract the parallel displacement movement, wherein following an initiation of the parallel displacement movement, the pivoting movement of the rear joint element with respect to the lower connecting joint element is substantially prevented at least partly by the coupling element.

2. A pivot device for use between parts of an orthopedic aid, comprising:

a multi-element kinematic joint chain having at least four joint elements, and rotation means connecting respective ones of said joint elements, wherein the elements connected with one another have a common rotational axis, and said rotation means are positioned parallel to one another, wherein said joint chain includes at least a first position representing full extension, said first position provides at least two different modes of joint flexion, in said first position, a first element of said joint elements performs a first type of movement and a second type of movement with respect to remaining joint elements of said joint elements connected to a first side of said first element, wherein said first type of movement, when initiated before said second type of movement, blocks said second type of movement and said second type of movement, when initiated before said first type of movement, blocks said first type of movement, a front joint element of said joint elements being pivotally coupled with an upper connecting joint element and a coupling element, a pivoting movement of the front joint element is substantially limited by at least one stop, a rear joint element of said joint elements being located substantially behind the front joint element in a walking direction, one end of the rear joint element is pivotally connected with the upper connecting joint element and the other end of the rear joint element is pivotally connected with a lower connecting joint element so that the rear joint element can perform a parallel displacement and a pivoting movement with respect to the coupling element in an initial position, a spring element, and at least a second stop, the spring element and the at least second stop counteract the pivoting movement and parallel displacement movement of the rear joint element, wherein following initiation of the parallel displacement movement, the pivoting movement of the rear joint element with respect to the lower connecting joint element is substantially prevented substantially partly by the pivoting connection of the rear joint element with the coupling element.

* * * * *